(12) United States Patent
Delio (10) Patent No.: US 11,083,440 B2
(45) Date of Patent: Aug. 10, 2021

(54) STREP THROAT TEST APPARATUS

(71) Applicant: JMDFNP, INC., Wilmette, IL (US)

(72) Inventor: Jean Marie Delio, Wilmette, IL (US)

(73) Assignee: JMDFNP, INC., Wilmette, IL (US)

(*) Notice: Subject to any disclaimer, the term of this patent is extended or adjusted under 35 U.S.C. 154(b) by 131 days.

(21) Appl. No.: 15/180,324

(22) Filed: Jun. 13, 2016

(65) Prior Publication Data

US 2017/0354399 A1  Dec. 14, 2017

(51) Int. Cl.
*A61B 10/00* (2006.01)
*A61B 5/08* (2006.01)
*A61B 5/097* (2006.01)
*A61B 5/00* (2006.01)
*A61B 5/145* (2006.01)

(52) U.S. Cl.
CPC .............. *A61B 10/00* (2013.01); *A61B 5/082* (2013.01); *A61B 5/097* (2013.01); *A61B 5/682* (2013.01); *A61B 5/6803* (2013.01); *A61B 5/14507* (2013.01); *A61B 5/14546* (2013.01); *A61B 2010/0087* (2013.01); *A61B 2562/0295* (2013.01)

(58) Field of Classification Search
CPC ............ G01N 33/497; G01N 33/56944; A61B 10/0096; A61B 10/0051; A61B 10/10; A61B 2010/0087; A61B 2562/0295; A61B 5/082; A61B 5/097; A61B 5/14507; A61B 5/14546; A61B 5/6803; A61B 5/682

See application file for complete search history.

(56) References Cited

U.S. PATENT DOCUMENTS

| | | | | |
|---|---|---|---|---|
| 6,565,808 B2* | 5/2003 | Hudak | ................. | B01L 3/5023 422/411 |
| 7,255,677 B2* | 8/2007 | Burch | ...................... | A61B 5/00 600/300 |
| 2007/0163588 A1* | 7/2007 | Hebrank | ................... | A61L 9/16 128/204.18 |
| 2009/0044597 A1* | 2/2009 | Kvasnik | ................. | A61B 5/097 73/23.3 |
| 2010/0324439 A1* | 12/2010 | Davenport | ............. | A61B 5/082 600/532 |
| 2016/0270693 A1* | 9/2016 | Bulbrook | ............... | A61B 5/097 |

* cited by examiner

*Primary Examiner* — Rajeev P Siripurapu
*Assistant Examiner* — Michael A Catina
(74) *Attorney, Agent, or Firm* — F. Chau & Associates, LLC (57) ABSTRACT

An apparatus for testing for streptococcal pharyngitis includes a tube having an open first end and a second end, and an opening on a side thereof, a dipstick inserted into the tube through the side opening, and an insert with a hole that can receive the dipstick and sized to nest the dipstick into the side opening of the tube. A swab at the end of the dipstick inside the tube receives microbes in a breath exhaled by a patient holding the first end of the tube to the patient's mouth. After being exhaled upon by the patient, the dipstick is removed for testing for the presence of microbes that cause streptococcal pharyngitis.

3 Claims, 10 Drawing Sheets

STREP THROAT TEST APPARATUS

BACKGROUND

Technical Field

Exemplary embodiments of the present disclosure are directed to an apparatus for testing for streptococcal pharyngitis, also known as strep throat.

Discussion of the Related Art

Strep throat is a common bacterial infection in children, being the cause of about 15-40% of sore throats among children, in addition to about 5-15% among adults. Symptoms of streptococcal pharyngitis include a sore throat, a fever of greater than 38 C (100 F), pus on the tonsils, and large cervical lymph nodes. Strep throat is most frequently caused by group A beta-hemolytic streptococcus (GAS), and is spread by respiratory droplets from an infected person, and may be spread directly or by touching something that has droplets on it and then touching the mouth, nose, or eyes.

Diagnostic tests for strep throat currently include a throat culture and a rapid strep test.

A throat culture, which evaluates for the presence of a bacterial infection in the throat, is generally considered to be the gold standard for the diagnosis of streptococcal pharyngitis, with a sensitivity of 90-95%. A sample from the throat is collected by swabbing the throat and is typically sent to a lab to grow a culture for further growth of possible GAS. If an organism grows, the culture is positive and the presence of an infection is confirmed. If no infection grows, the culture is negative.

The rapid strep test (RST), or rapid antigen detection test (RADT), is quicker than a throat culture, and has a statistically equal specificity (98%) as a throat culture, but has a lower sensitivity (70%). There are currently several types of rapid strep test in use, each employing a distinct technology. However, they all work by detecting the presence of GAS in the throat of a patient by responding to GAS-specific antigens on a throat swab. These tests are 99 percent accurate.

A microbial culture from a throat swab is a reliable but not necessarily affordable alternative to an RST which has high sensitivity and specificity. However, a culture requires special facilities and usually takes 48 hours to give a result, whereas an RST can give a result within several minutes.

A patient's throat is first swabbed to collect a sample of throat secretions. In most RSTs, this secretion sample is then exposed to a reagent containing antibodies that will bind specifically to a GAS antigen. A positive result is signified by a certain visible reaction. A positive throat culture or RADT in association with symptoms establishes a positive diagnosis in those in which the diagnosis is in doubt. Although in adults, a negative RADT is usually sufficient to rule out the diagnosis, in children, a throat culture is recommended to confirm the result. However, obtaining a throat culture from a patient can be challenging, as many patients are sensitive to having their throats swabbed, and the swabbing can trigger a patient's gag reflex.

SUMMARY

According to an embodiment of the disclosure, there is provided an apparatus for testing for streptococcal pharyngitis that includes a tube having an open first end and a second end, and an opening on a side thereof, a dipstick inserted into the tube through the side opening, and an insert with a hole that can receive the dipstick and is sized to nest and secure the dipstick into the side opening of the tube. A swab at an end of the dipstick inside the tube receives microbial secretions in a breath forcibly exhaled by a patient whose mouth is sealed around the first end of the tube, and after being forcible exhaled upon by the patient, the dipstick is removed for testing for the presence of microbes that cause streptococcal pharyngitis.

According to further embodiments of the disclosure, the second end is closed off.

According to further embodiments of the disclosure, the closed second end includes a plurality of air holes.

According to further embodiments of the disclosure, the second end is closed off by a face mask filter.

According to further embodiments of the disclosure, the apparatus includes a cup inserted into the second end, the cup including include a plurality of holes through which a patient's breath is discharged from the tube.

According to further embodiments of the disclosure, the cup further includes a filter that restricts microbes.

According to further embodiments of the disclosure, the tube is made of cardboard, and the cup and the insert are made of plastic.

According to further embodiments of the disclosure, the dipstick includes a line indicative of where the dipstick is positioned.

DETAILED DESCRIPTION OF EXEMPLARY EMBODIMENTS

Exemplary embodiments of the disclosure as described herein generally provide an apparatus and method for testing for streptococcal pharyngitis. While embodiments are susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

Figure 1:
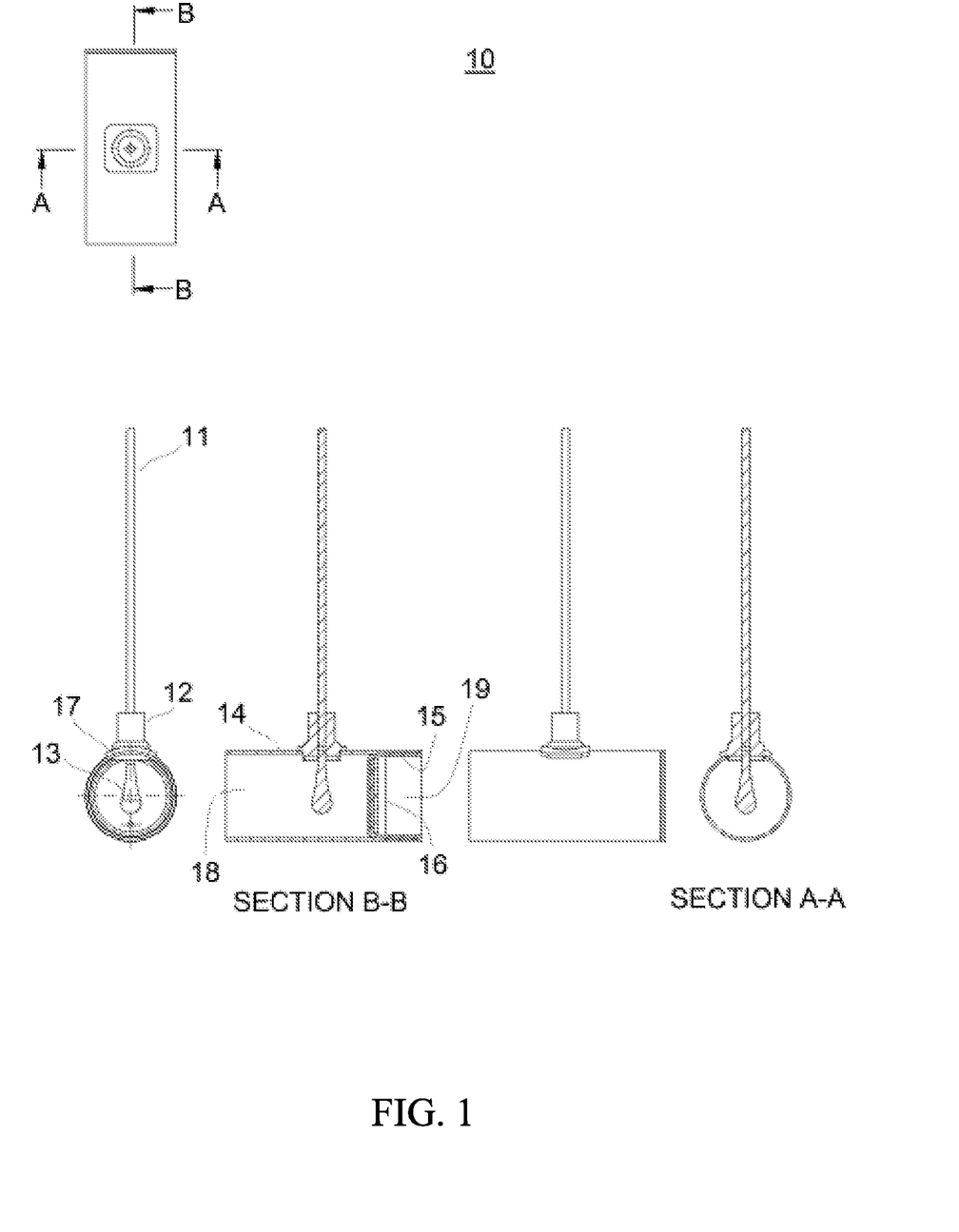
FIG. 1 is an orthographic view of a strep throat test apparatus according to an embodiment of the disclosure.
Figure 2:
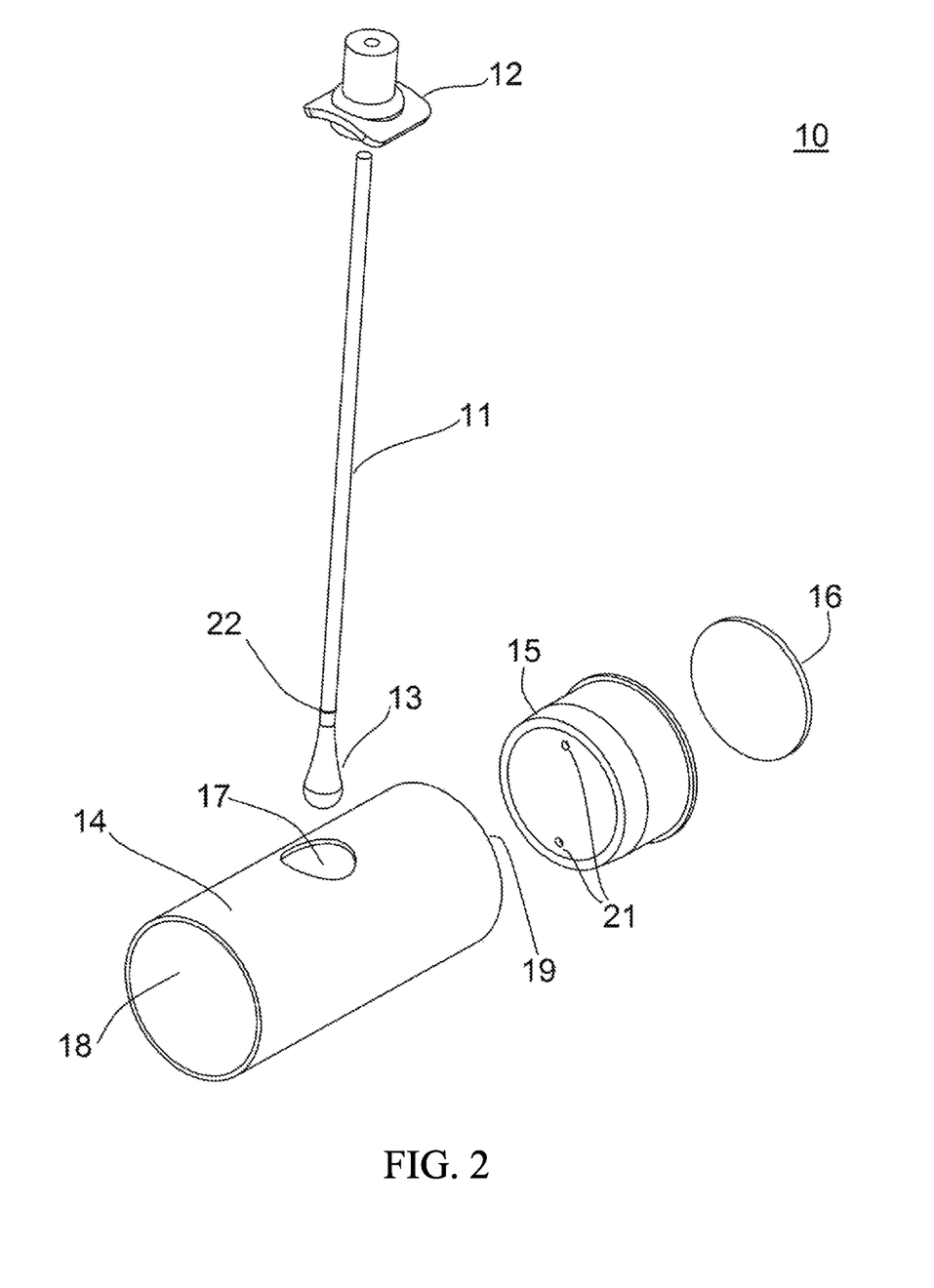
FIG. 2 is an exploded view of a strep throat test apparatus according to an embodiment of the disclosure.

FIG. 1 is an orthographic projection of a strep throat test apparatus 10 according to an embodiment of the disclosure that shows product views and cutaway section views, and FIG. 2 is an exploded view of the same. A strep throat test apparatus 10 according to an embodiment of the disclosure may be referred to as a strepalyzer. Referring to FIG. 1, a top view of the strep throat test apparatus 10 is shown in the upper left, an end view looking though the strep throat test apparatus 10 is shown at the lower left, a side view cut away along section B-B is shown second from the lower left, a side view is shown second from the lower right, and an end view cut-away along section A-A is shown at the lower right.

Referring to FIGS. 1 and 2, the strep throat test apparatus 10 according to an embodiment of the disclosure includes a disposable tube 14, a dipstick 11 with a swab 13 at one end that is wider than the shaft of the dipstick 11. The dipstick 11 can be inserted into the tube 14 through a hole 17 in the side of the tube 14, and the strep throat test apparatus 10 further includes an insert 12 that surrounds the dipstick 11 and seals and secures the dipstick into the hole 17. The swab 13 may be covered with a material that can absorb the patient's throat secretions. The insert 12 slides on from the end of the dipstick 11 to below a line 22 and nests into the hole 17 in the tube 14 to hold the dipstick 11 in place. The tube also includes an open first end 18, and a second end 19 opposite the first end 18. In some embodiments, the second end 19 is closed, but has a plurality of air holes 21 to allow air to pass through, while in other embodiments, the second end 19 is open into which an end cup 15 is inserted. The end cup 15 also includes a plurality of air holes 21 to allow air to pass through, and includes a filter 16 to restrict microbes from escaping. An exemplary, non-limiting number of air holes is two (2). The filter can be made from any suitable material as is known in the art. If the tube 14 has a closed second end 19, the filter 16 may also be inserted into the tube 14 to be positioned between the hole 17 and the second end 19. In other embodiments, the filter may be made of a material such as is used for face masks. In this embodiment, the filter 16 itself can be used to close off the second end 19. The tube 14, the end cup 15, the filter 16, and the insert 12 are intended to be disposable. For example, the tube 14 can be made of cardboard, and the insert 12 and end cup 15 can be made of plastic.

FIGS. 3-10 illustrate steps in using a strep throat test apparatus 10 according to an embodiment of the disclosure to detect strep throat.

Figure 3:
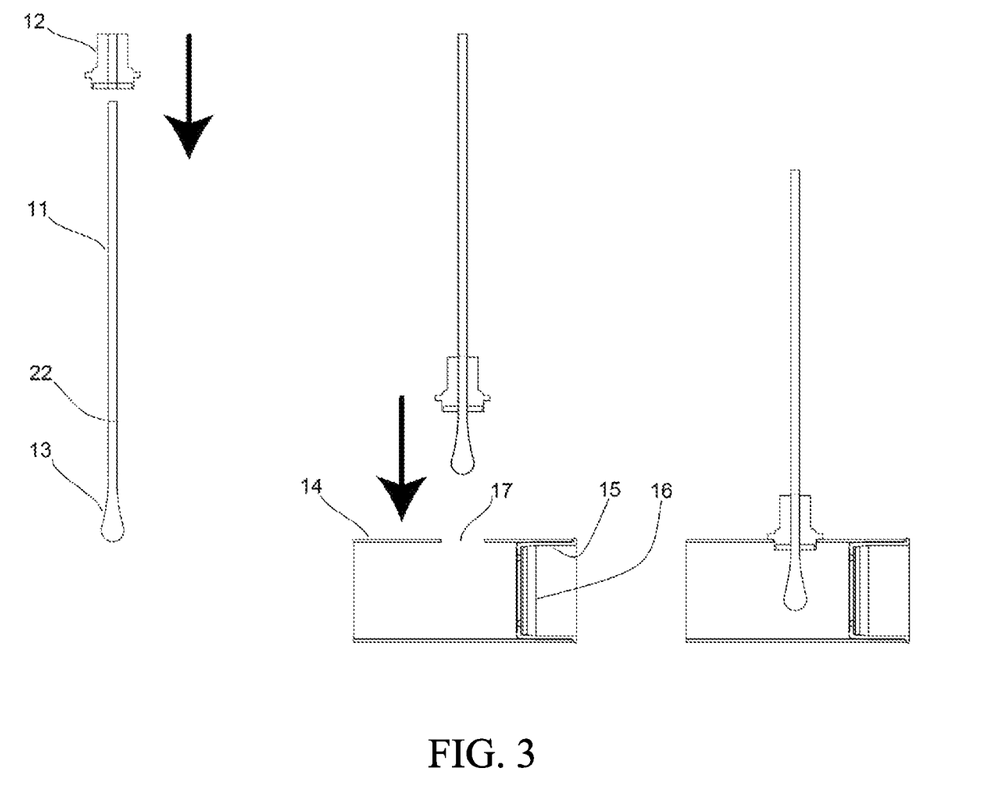
FIGS. 3-10 illustrate steps in the use of a strep throat test apparatus according to an embodiment of the disclosure to detect strep throat.
Figure 4:
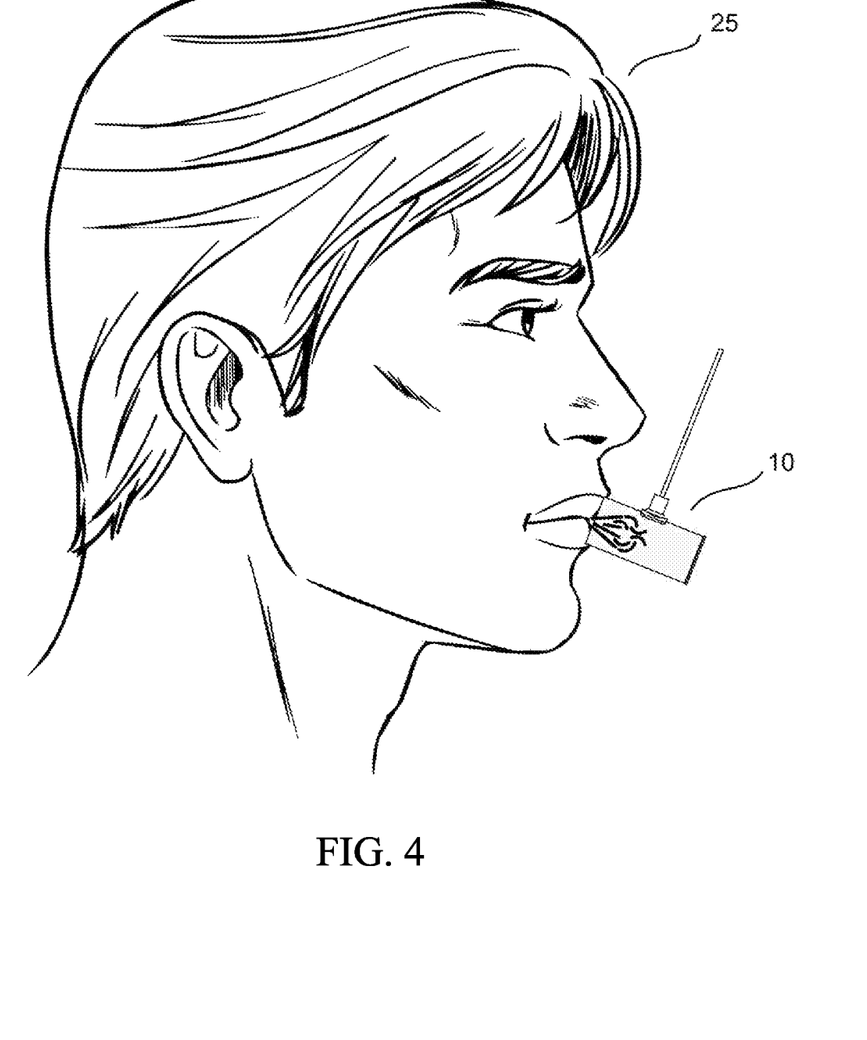
Figure 5:
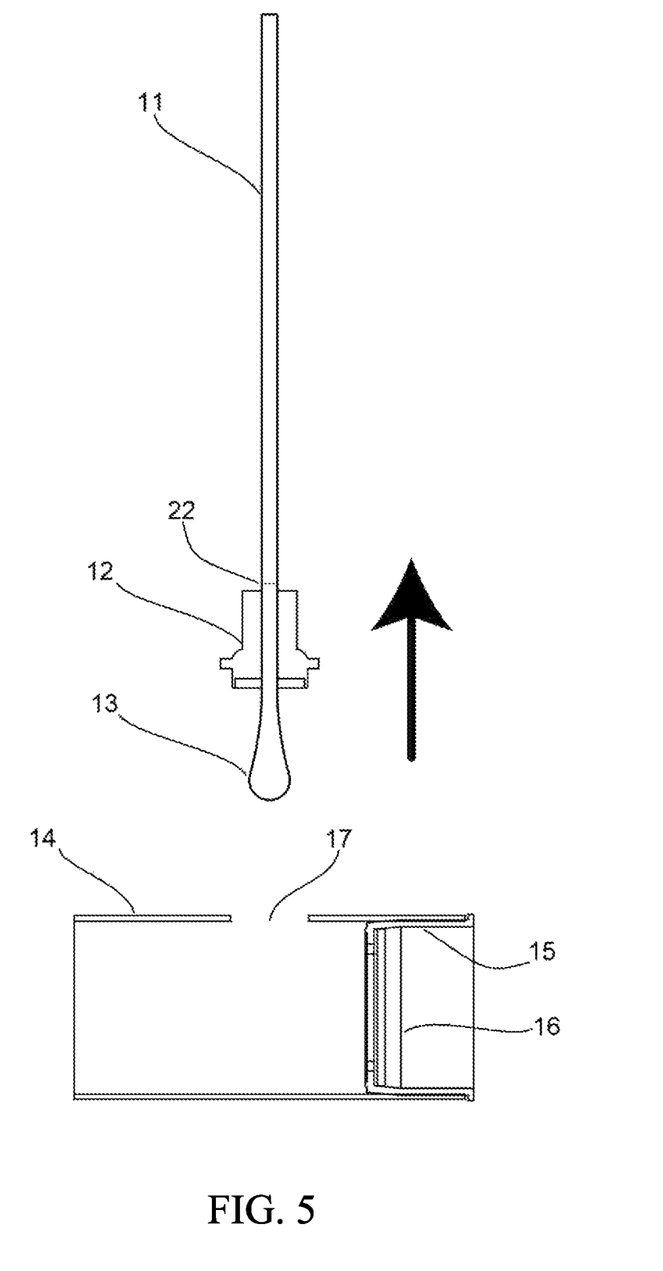
Figure 6:
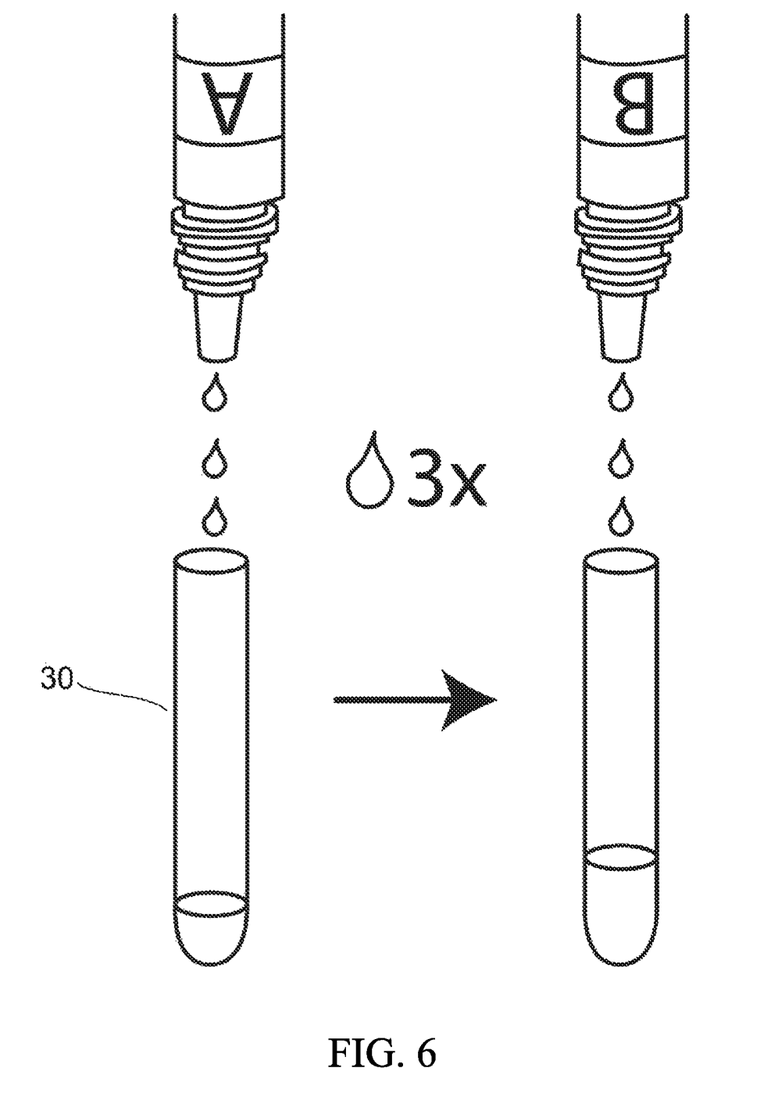
Figure 7:
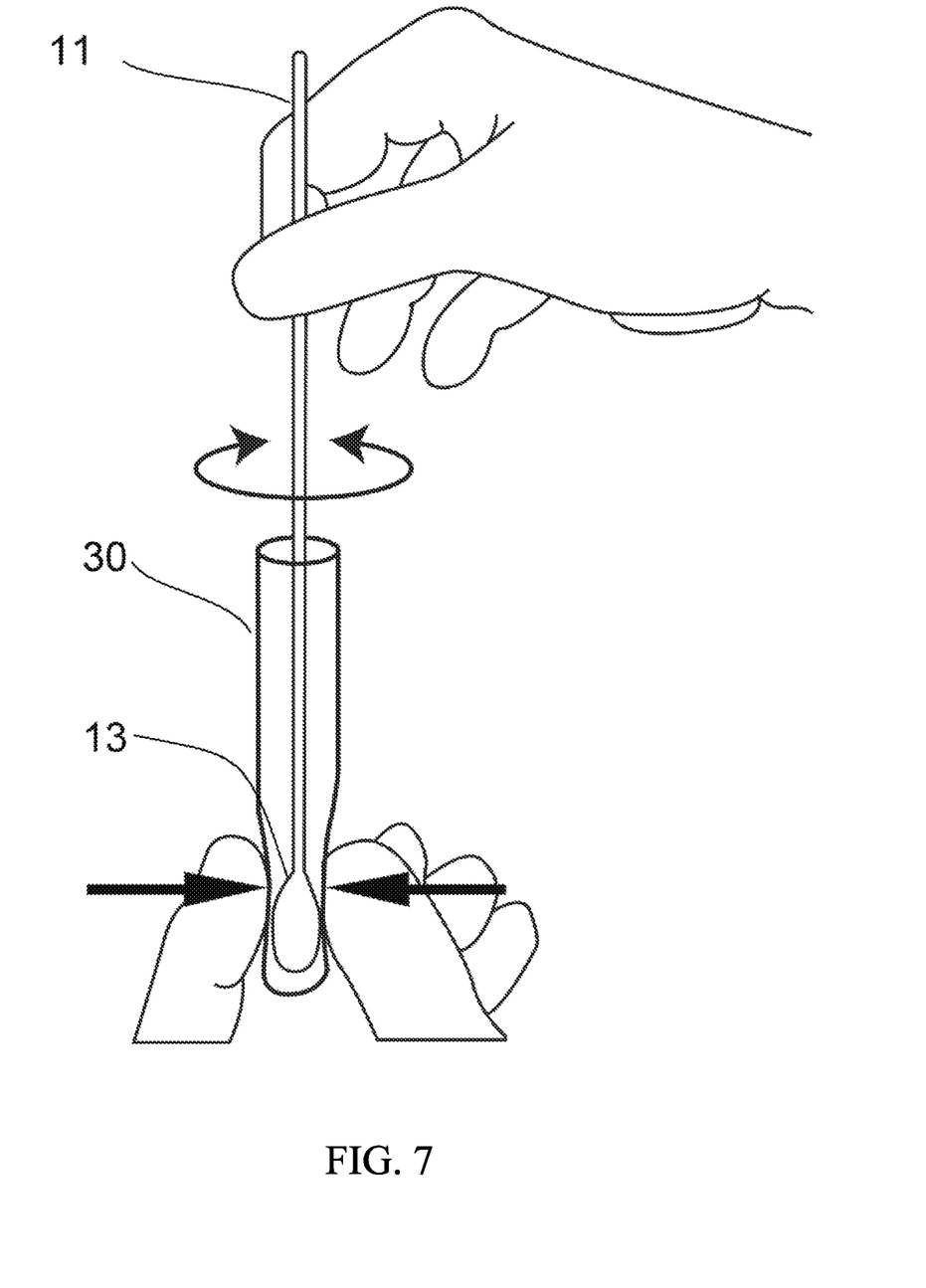
Figure 8:
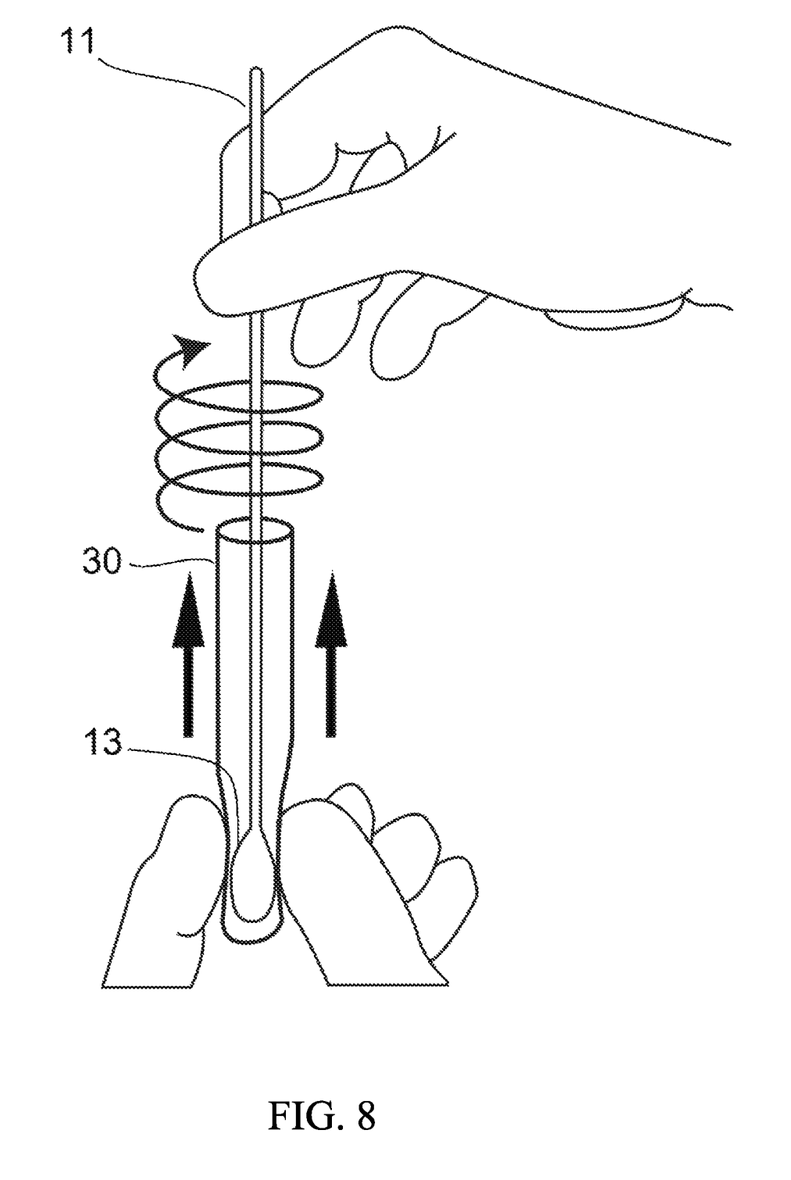
Figure 9:
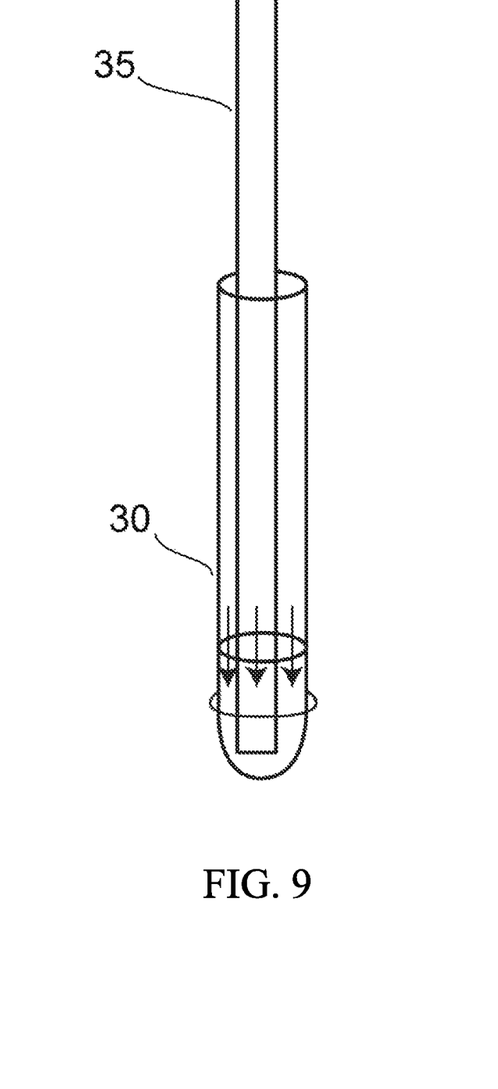
Figure 10:
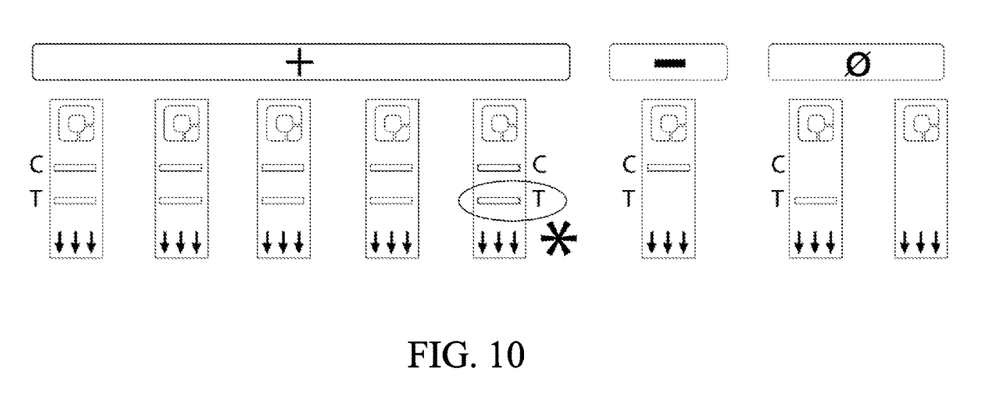

FIG. 3 depicts, from left to right, the plastic insert 12 sliding onto the dipstick 11 in the direction of the arrow, and the insertion of the dipstick 11 and insert 12 into the cardboard tube 14 in the direction of the arrow securely for testing. FIG. 4 shows a patient 25 blowing or forcibly exhaling into the tube 14, coating the swab 13 with microbes from the patient's throat secretions. The air holes 21 in the end cup 15 allow the air received from the blowing patient to be discharged, while the filter 16 traps microbes in the patient's secretions. FIG. 5 shows the dipstick 11 and insert 12 being removed in the direction of the arrow for testing. FIG. 6 shows the placement of two reagents to into a clean test tube 30, for testing purposes. An exemplary, non-limiting test tube 30 is compressible. According to an embodiment, three (3) drops of Reagent A and three (3) drops of Reagent B are added into a clean test tube 30. Reagents A and B are well known in the art of testing for strep throat. This solution should turn green. Next, as shown in FIG. 7, the patient dipstick 11 and sample is added to the test tube 30. According to an embodiment, the dipstick 11 is rotated a number of times, as indicated by the spiral, and after a period of time, the bottom of the test tube 30 should be squeezed in the direction of the arrows to compress the swab 13. The period of time may be about one minute. According to an embodiment, the swab may be rotated a minimum of five (5) times. Then all liquid is expressed from the swab 13 against the inside of the test tube 30, as indicated by the arrows and shown in FIG. 8, and the dipstick 11 is removed from the test tube 30 while squeezing the swab 13 firmly. The dipstick 11 may now be discarded. Next, as shown in FIG. 9, a test strip 35 as is known in the art is placed in the tube 30, and the test strip 35 is rotated. After a short duration of time, the test strip 35 can be read. According to an embodiment, the test strip result can be read after 5 minutes, although some positive results may appear sooner. FIG. 10 shows some examples of test results, including a positive results and a negative result. The test strip includes a blue control line C, and a test line T. The test line will initially be substantially invisible, and will turn pink if the group A beta-hemolytic streptococcus that causes strep throat is present. The test strips under the "+" block show a visible, pink test line. The test strip under the "−" block shows a negative result, in that no test line appeared. The test strips under the "Ø" symbol are invalid, as there is no control line in these strips.

While embodiments of the present disclosure have been described in detail with reference to exemplary embodiments, those skilled in the art will appreciate that various modifications and substitutions can be made thereto without departing from the spirit and scope of the invention as set forth in the appended claims.

What is claimed is:

1. A method for obtaining samples for testing for streptococcal pharyngitis, consisting the steps of:
    exhaling, by a patient, a breath into an apparatus being held in one of the patient's hands, wherein the apparatus consists of a single, hollow cylindrical tube that has an open first end, an open second end, an opening on a side thereof, a removable insert placed in the side opening, a dipstick held in place by the removable insert and inserted into the hollow cylindrical tube through the side opening, a swab at the end of the dipstick, and face mask filter material inserted into the open second end, wherein the face mask filter material is configured to trap particulate matter and pass air;
    receiving, by the swab, microbial throat secretions in the breath forcibly exhaled by the patient, wherein the patient's mouth is sealed around the open first end of the tube;
    removing the dipstick for testing the swab for the presence of microbes that cause streptococcal pharyngitis; and
    disposing of the apparatus after removing the dipstick, wherein said entire apparatus is sized to correspond to a size of a human hand.

2. A method for obtaining samples for testing for streptococcal pharyngitis, consisting the steps of:
    exhaling by a patient, a breath into an apparatus being held in one of the patient's hands, wherein the apparatus consists of a single, hollow cylindrical tube that has an open first end, an open second end, an opening on a side thereof, a removable insert placed in the side opening, a dipstick held in place by the removable insert and inserted into the hollow cylindrical tube through the side opening, a swab at the end of the dipstick, and a cup inserted into the open second end, the cup consisting of a plurality of holes through which a patient's breath is discharged from the hollow cylindrical tube and a filter that restricts microbes:
        receiving, by the swab, microbial throat secretions in the breath forcibly exhaled by the patient, wherein the patient's mouth is sealed around the open first end of the tube;
        removing the dipstick for testing the swab for the presence of microbes that cause streptococcal pharyngitis; and
        disposing of the apparatus after removing the dipstick, wherein said entire apparatus is sized to correspond to a size of a human hand.

3. The method of claim 2, wherein the hollow cylindrical tube is made of cardboard, and the cup is made of plastic.

* * * * *